United States Patent [19]

Shave

[11] Patent Number: 4,603,538

[45] Date of Patent: Aug. 5, 1986

[54] METHOD OF PREPARING A DOUBLE STERILE PACKAGE

[75] Inventor: William H. Shave, Amityville, N.Y.

[73] Assignee: Pfizer Hospital Products Group, Inc., New York, N.Y.

[21] Appl. No.: 671,727

[22] Filed: Nov. 15, 1984

[51] Int. Cl.[4] .................. B65B 31/02; B65B 55/10; B65B 55/18

[52] U.S. Cl. .................................. 53/425; 53/434; 53/449

[58] Field of Search ............... 53/425, 428, 432, 433, 53/434, 449, 477; 156/290, 291; 206/63.3

[56] References Cited

U.S. PATENT DOCUMENTS 2,917,878 12/1959 Carnarius et al. .............. 53/434 X
3,726,057 4/1973 Kemble ............................ 53/425
3,815,315 6/1974 Glick ................................. 53/21
3,938,659 12/1976 Wardwell ...................... 53/425 X

*Primary Examiner*—Robert L. Spruill
*Assistant Examiner*—Michael D. Folkerts
*Attorney, Agent, or Firm*—Charles J. Knuth; Peter C. Richardson; Lorraine M. Donaldson

[57] ABSTRACT

A method of preparing a sterile double package by inserting a sterile article into an inner package which has been sealed on three sides, inserting the inner package into an outer package which has three sides sealed, sealing the remaining side of the outer package to form a double package, sterilizing the contents of the outer package, and sealing the fourth side of the inner package through the outer package.

4 Claims, 6 Drawing Figures

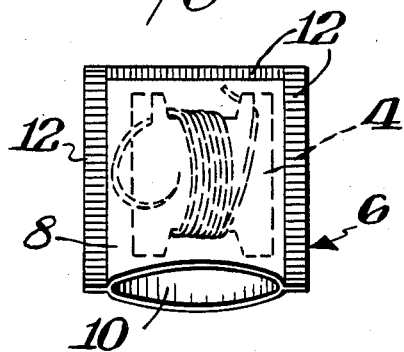
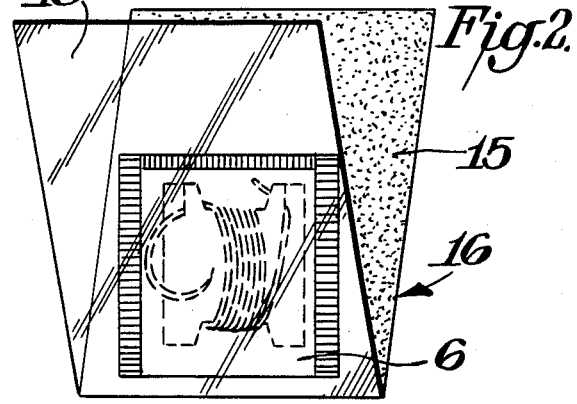
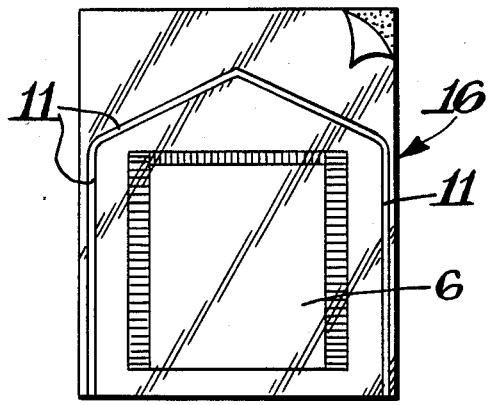
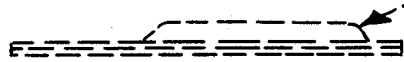
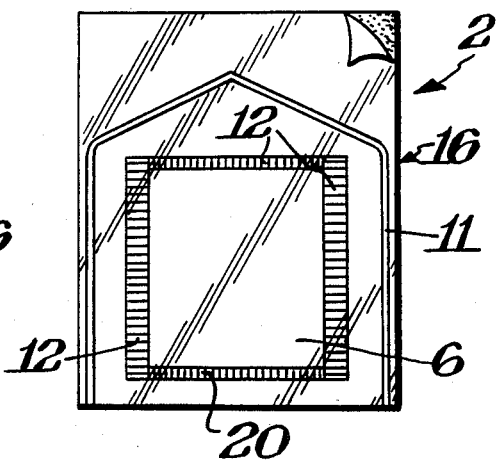

METHOD OF PREPARING A DOUBLE STERILE PACKAGE

BACKGROUND OF THE INVENTION

The present invention relates to a novel process for preparing a double sterile package. More particularly, it relates to sealing an inner package through a sealed outer package while allowing the sealed inner package free movement in the outer package.

Sterile packages intended for use in sterile zones must meet exacting requirements. The sterilized condition within and without the inner package must be maintained while the entry of contaminants into the packages must be prevented. The package must be able to resist variations in environmental conditions. Additionally, the sterile package must be able to be easily and quickly opened, without recourse to implements, thereby permiting the ready removal of the sterile contents without disrupting the sterility thereof.

Current methods used to prepare double sterile packages include sterilizing an inner package open on one end. The wrapped sterile package is then dried in an oven and stored in a dry area, i.e., an environment free from moisture, until the final sealing of this inner package takes place in a clean room using aseptic techniques, where the package is again sterilized before being heat sealed. Thus, the numerous steps in this process and the need for a dry area and a sterile area, are both costly and time consuming. This lengthy procedure can adversely effect the quality of the contents as well as possible risk of contamination.

U.S. Pat. No. 3,815,315 discloses a sterile package whose gaseous contents are either evacuated or replaced with inert gas prior to sealing. The package is then held in a dry room area, and subsequently sterilized in a sterile area commonly called a clean room before the final sealing step.

There remains a need for an efficient and economical method of preparing a sterile double package.

SUMMARY OF THE INVENTION

The present invention relates to a method of preparing a sterile double package including a generally rectangular sealed inner package containing a sterile surgical article and comprising two opposed sealable layers of material sealed adjacent their peripheries and a generally rectangular sealed outer package totally surrounding the inner package and comprising two opposed sealable layers of material sealed adjacent their peripheries with at least one of the opposed layers being vapor permeable, the inner package not being constrained from movement with the outer package.

The method of preparing a sterile double package includes inserting a surgical article into the inner package, the inner package being sealed on three sides and open on the fourth. The inner package is then inserted between the opposed layers of the outer package, with no more than three sides of the layers of the outer package being sealed. The remaining sides of the outer package are then sealed to totally enclose the inner package, thereby forming a double package. The contents of the outer package are sterilized by a perfusion of a sterilizing gas through a vapor permeable layer, and placed under a vacuum to remove the gas vapor. The fourth side of the inner package is then sealed adjacent the periphery thereof through the outer package. The conditions of the sealing operation of the fourth side of the inner package and the materials of the opposed layers of the inner and outer package are such that neither layer of the outer package is sealed to the adjacent layer of the inner package and the opposed layers of the outer package are not further sealed together during the sealing operation of the fourth side of the inner package.

The materials of the inner package is preferably, a foil laminate. The material of the outer package is preferably composed of a high grade surgical paper with polypropylene laminated film.

The present invention also embraces a method for preparing a sterile double package of the type previously described wherein a suture is first inserted into an inner package. The inner package is comprised of foil laminate, and is sealed on three sides and open on the fourth. The inner package is then inserted into an outer package.

The outer package is comprised of a layer of high grade surgical paper and a layer of polypropylene laminated film and is sealed on no more than three sides. The fourth side of the outer package is sealed by heating at a temperature of from about 275° C. to 325° thereby totally enclosing the inner package to form a double package. The double package contents are sterilized by a perfusion of ethylene oxide gas through the high grade surgical paper layer of the outer package, and placed under vacuum. In the final step, the fourth side of the inner package is sealed, adjacent the periphery, by heating at about 200° C. to 250° C.

The present invention also embraces the sterile double package produced by the above described method.

BRIEF DESCRIPTION OF THE DRAWINGS

Novel features and advantages of the present invention, in addition to those mentioned above, will become apparent from a reading of the following detailed description in conjunction with the accompanying drawings, wherein:

FIG. 1 is a top plan view of the surgical article in the inner package which is sealed on three sides of the present invention.

FIG. 2 is a top plan view of the open inner package in the open outer package.

FIG. 3 is a top plan view of the open inner package in the sealed outer package.

FIG. 4 is a side elevational view of the double package being sterilized.

FIG. 5 is a side elevational view of the double package under vacuum.

FIG. 6 is a top plan view of the sealed fourth side of the inner package through the outer package.

DESCRIPTION OF THE PREFERRED EMBODIMENT

A particularly useful product made by the method of this invention is a sterile double package in which the inner package is sealed through the outer package. The layers of the outer package, however are not sealed to the inner package, nor are the layers sealed together. The resulting double package contains an inner package that is not constrained from movement within the outer package. The method of this invention is well suited to the production of such a sterile double package.

FIGS. 1-6 illustrate the steps in a preferred method for making a sterile double package.

In FIG. 1 is shown the first step in preparing a sterile double package 2 including inserting a sterile surgical article 4 into an inner package 6. The sterile surgical article can be, for example, a sterile suture.

The inner package 6 is generally rectangular, with the size of the package being a function of the size of the surgical article 4. The inner package 6 comprises two opposed sealable layers 8, 10 of material. The two layers 8, 10 may be made of different compatible materials, or of the same material. By compatible materials is meant materials that have sealing temperatures within the same range. Preferred materials for the package 6 having different compatible materials are a lamination of polyester, foil and adhesives, preferably with low temperature adhesives. Preferred materials for the inner package 6 using the same material is foil laminate with low temperature adhesives. Preferably, each foil laminate layer is 1.5 mil thick.

Other suitable materials for the inner package are polyester low temperature adhesive laminations.

The inner package 6 is sealed on three sides and open on the fourth. The sealing temperature is determined by the type of material used. For example, foil laminate is sealed at 200° to 250° C. The layers 8, 10 of the inner package 6 are sealed adjacent their peripheries 12.

In FIG. 2, the inner package 6, containing the surgical article, which is sealed on three sides and open on the fourth side, is inserted between the opposed layers 13, 15 of the outer package.

The outer package 16 is generally rectangular, with the size of the outer package 16 being a function of the size of the inner package 6. The outer package comprises two opposed sealable layers 13, 15. The two opposed sealable layers 13, 15 of the outer package 16 are sealed adjacent their peripheries 11 on three sides and open on the fourth.

The two layers 13, 15 of the outer package material are selected to impart strength and flexibility to the package. At least one layer of the outer package must be significantly vapor permeable for efficient sterilization of the outer package contents. Preferably materials are high grade surgical paper with polypropylene laminated film. Surgical paper used for the outer package is preferably 40 to 50 pound Kraft about 3.5 mil in thickness while the polypropylene laminated film outer layer is about 3 mil. in thickness.

Other suitable materials for the outer package are coated or uncoated Tyvek ® or coated paper sealed to polypropylene laminates, or other suitable supported film with a high temperature adhesive.

In FIG. 3, after the inner package 6 is inserted, the fourth side of the outer package 16 is sealed totally enclosing the inner package 6 and forming the double package 2. The sealing temperature of the outer package layers is determined by the type of material used. For example, high grade surgical paper and a layer of polypropylene laminated film is sealed by heating at from about 275° C. to 325° C.

The seals used in the present invention may be obtained by using conventional sealing techniques. Preferably a band sealer is used whereby the double package 2 is threaded through the band sealer and jaws apply the proper combination of temperature and pressure creating the desired seal. Other suitable sealing techniques include drop heated bar sealers, and rolling and crown die sealers. The present invention, however, is not limited to any particular method of sealing technique, and any convenient method producing the proper combination of temperature and pressure is suitable.

In FIG. 4, the contents of the double package 2 are sterilized by perfusion of the sterilizing gas through the vapor permeable layer of the outer package 16. The sterilization can be done in any conventional manner. Following the sterilization step the double package 2 is placed under vacuum, using any conventional vacuum method to remove residual gas.

Preferably, the double package 2 is sterilized by placing the package in a suitable ethylene oxide sterilizing oven. The oven is evacuated after which a mixture of 12 percent by volume ethylene oxide and 88 percent by volume dichlorodifluoromethane (Freon 12) is admitted to the oven. The oven pressure is preferably about 20 PSIG, the temperature is from about 70° to 120° C., and the gas exposure time is from about 6 to 10 hours.

After the gas has been in contact with the double package 2 mixture for at least 6 hours, and preferably 8 hours, the double package 2 is removed from the sterilizating oven and placed in a vacuum drying oven. The oven is heated to a temperature of from about 100° C. to 120° C. for a minimum of 24 hours under a 27 inch vacuum.

FIG. 6 shows the final sealing operation whereby the fourth side of the inner package 6 is sealed through the outer package 16. The fourth side of the inner package 6 is sealed adjacent the periphery 20 thereof, through the outer package 16.

The materials of construction of the double package 2 are chosen such that when the inner package 6 is sealed through the outer package 16, due to the difference between the sealing temperature of material of the inner package 6, the outer package 16 will not be sealed to the inner package 6.

For example, if the inner package 6 material is foil laminate with a sealing temperature of from about 200° C. to 250° C., and the outer package 16 material is a layer of high grade surgical paper and a layer of polypropylene laminated film with a sealing temperature of from about 275° C. to 325° C., the fourth side of the inner package will be sealed at about 220° C. to 250° C.

Sealing the inner package in this manner will provide the desired result that neither layer of the outer package 16 will be sealed to the adjacent layer of the inner package 6. Also, the opposed layers of the outer package 16 will not be sealed together during the sealing operation of the sealing of the fourth side of the inner package 6, and the inner package 6 will not be constrained from movement within the outer package 16.

The sterile double package method of this present invention eliminates many of the problems of previously used methods of sterilization of double packages. The method provides a relatively simple economical time saving system, eliminating the step of sterilizing the open inner package, drying and storing under sterile conditions and then sealing the fourth side of the inner package in a clean room under aseptic conditions. It also eliminates the need to place the sealed inner package into an outer package and complete a second sterilization cycle exposing the contents to adverse conditions a second time. Our method eliminates the costly clear room, the aseptic handling procedure, the second sterilization, the crushing and the deforming of sutures in sealed paks under sterilizing pressures, the possibility of change contamination and a very marked savings in time.

It will be appreciated that sterile packages can be made by this method for many different uses. Further modification will occur to those skilled in the art. For example, the four sides of the outer package can be sealed at one time thereby eliminating the two step process. In this embodiment, the inner package is placed on one layer of the outer package and the second layer of the outer package is positioned and sealed in one step.

The scope of the invention is defined by the appended claims and should not be understood as limited by the specific embodiments described herein.

I claim:

1. A method of preparing a sterile double package including (1) a generally rectangular sealed inner package containing a sterile surgical article and comprising two opposed sealable layers of material sealed adjacent their peripheries and (2) a generally rectangular sealed outer package totally surrounding said inner package and comprising two opposed sealable layers of material sealed adjacent their peripheries with at least one of said opposed layers being vapor permeable, said inner package not being constrained from movement within said outer package, comprising the steps of
   (a) inserting a surgical article into said inner package, said inner package being sealed on three sides and open on the fourth side;
   (b) inserting said inner package between said opposed layers of said outer package, with no more than three sides of said layers of the outer package being sealed, and then sealing the remaining sides of the outer package to totally enclose the inner package to form a double package;
   (c) sterilizing the contents of the outer package by perfusion of a sterilizing gas through said vapor permeable layer thereof;
   (d) removing gas vapors through vacuum, and,
   (e) sealing the fourth side of the inner package adjacent the periphery thereof through the outer package,
with the conditions of the sealing operation of said step (e) and the materials of said opposed layers of said inner and outer packages being such that neither layer of said outer package is sealed to the adjacent layer of said inner package and said opposed layers of said outer package are not further sealed together during the sealing operation of said step (e).

2. The method of claim 1 wherein the material of inner package is foil laminate.

3. The method of claim 1 wherein the material of the outer package is comprised of one layer of high grade surgical paper and one layer of polypropylene laminated film.

4. A method of preparing a sterile double package including (1) a generally rectangular sealed inner package containing a sterile surgical article and comprising two opposed sealable layers of material sealed adjacent their peripheries and (2) a generally rectangular sealed outer package totally surrounding said inner package and comprising two opposed sealable layers of material sealed adjacent their peripheries with at least one of said opposed layers being vapor permeable, said inner package not being constrained from movement within said outer package, comprising the steps of:
   (a) inserting a suture into an inner package, said inner package comprised of foil laminate said inner package being sealed on three sides and open on the fourth side;
   (b) inserting said inner package into an outer package, said outer package comprised of one layer of high grade surgical paper and one layer of polypropylene laminated film, said outer package being sealed on no more than three sides;
   (c) sealing the remaining sides of said outer package at a temperature of from about 275° C. to 325° C. enclosing the inner package to form a double package;
   (d) sterilizing the contents of the outer package by a perfusion of ethylene oxide gas through the high grade surgical paper layer thereof,
   (e) removing gas vapors by placing the double package under vacuum; and,
   (f) sealing the fourth side of the inner package adjacent the periphery thereof through the outer package, said sealing temperature of from about 200° C. to 250° C.

* * * * *